US006451608B1

(12) United States Patent
Kikuchi (10) Patent No.: US 6,451,608 B1
(45) Date of Patent: Sep. 17, 2002

(54) METHOD FOR MEASURING AMOUNT OF ACTIVE OXYGEN PRODUCED BY LEUKOCYTES AND OXIDATIVE STRESS (75) Inventor: Yuji Kikuchi, Ryugasaki (JP)

(73) Assignee: Director of National Food Research Institute, Ministry of Agriculture, Forestry and Fisheries, Tsukuba (JP)

( * ) Notice: Subject to any disclaimer, the term of this patent is extended or adjusted under 35 U.S.C. 154(b) by 0 days.

(21) Appl. No.: 09/490,450

(22) Filed: Jan. 24, 2000

(30) Foreign Application Priority Data

Aug. 9, 1999 (JP) ............................................. 11-225522

(51) Int. Cl.⁷ ............................................. G01N 33/48
(52) U.S. Cl. ........................... 436/63; 436/68; 436/164; 436/165; 436/172; 435/2; 435/4; 435/29; 422/52
(58) Field of Search ............................... 436/56, 63, 68, 436/136, 164, 165, 172; 435/2, 4, 29; 422/52, 55, 58, 82.05

(56) References Cited

U.S. PATENT DOCUMENTS

| 5,023,054 | A |   | 6/1991  | Sato et al. ............. | 422/82.09 |
|-----------|---|---|---------|--------------------------|-----------|
| 5,912,179 | A | * | 6/1999  | Alvarez et al. ........... | 436/63    |
| 6,133,039 | A | * | 10/2000 | Heinecke ................. | 436/89    |
| 6,165,797 | A | * | 12/2000 | Halstead ................. | 436/128   |
| 6,218,130 | B1| * | 4/2001  | Lamb .................... | 435/7.21  |

FOREIGN PATENT DOCUMENTS

| JP | 2-130471 |   | 5/1990  |
|----|----------|---|---------|
| JP | 3-257366 | * | 11/1991 |
| JP | 2532707  |   | 6/1996  |

OTHER PUBLICATIONS

Kikuchi et al. Proc. SPIE–Int. Soc. Opt. Eng., vol. 2978, pp. 165–171, 1997.*
Kikuchi. *Microvascular Research,* vol. 50, pp. 288–300, 1995.*
Kikuchi et al. *Microvascular Research,* vol. 47, pp. 126–139, 1994.*
"Standardization of Measurement of Oxidative Stress of Blood Samples by Detection of Luminol Enhancing Chemiluminescence—Aiming at Monitoring Time Course of in Vivo Oxidative Stress," Journal of Japanese Pharmacology, vol. 111, No. 3, 1998, pp. 177–186. (with English Abstract).

* cited by examiner

*Primary Examiner*—Maureen M. Wallenhorst
(74) *Attorney, Agent, or Firm*—Oblon, Spivak, McClelland, Maier & Neustadt, P.C.

(57) ABSTRACT

A method for measuring luminol enhancing light emission without separating leukocytes and erythrocytes, that is, using whole blood and a method for measuring the number of leukocytes trapped by the capillary bed or the time required for leukocytes to pass through the capillary bed to thereby provide an effective index for ability of leukocytes to protect infection and for oxidative stress caused by leukocytes are provided. Specifically, a method is provided for measuring an amount of active oxygen produced by leukocytes and oxidative stress, where the method includes allowing an anticoagulated whole blood sample collected from a human or an animal to pass through a microchannel array including a substrate with a fine channel array arranged on its surface and a transparent substrate which is adhered onto the substrate by contact bonding, and measuring a light emission level from whole leukocytes passing through the microchannel array through the transparent substrate to use the measured light emission level as an index of an amount of active oxygen produced by leukocytes and oxidative stress.

12 Claims, 6 Drawing Sheets

METHOD FOR MEASURING AMOUNT OF ACTIVE OXYGEN PRODUCED BY LEUKOCYTES AND OXIDATIVE STRESS

FIELD OF THE INVENTION

The present invention relates to a method for measuring an amount of active oxygen produced by leukocytes and oxidative stress, more specifically to a method for measuring an amount of active oxygen produced by leukocytes and oxidative stress, and a method for assessing an effect of a substance selected from the group consisting of drugs, foods, and substances made from their ingredients to enhance or suppress an amount of active oxygen produced by leukocytes and oxidative stress.

BACKGROUND OF THE INVENTION

Production of active oxygen by leukocytes is inevitable for killing bacteria. A high active oxygen-productive capability of leukocytes is very important for protection against infection. Active oxygen is, however, known to damage tissues and DNA. For example, ischemia reperfusion injury is thought to be caused by active oxygen, which would probably be produced by leukocytes.

In order to prevent diseases, it is very important to measure an amount of active oxygen produced by leukocytes, and, to develop a method for increasing or decreasing, case by case, the amount of produced active oxygen.

Luminol enhancing light emission is widely used at the laboratory level for measurement of an amount of active oxygen produced by leukocytes. This method is performed by measuring faint light emitted from luminol when it is oxidized by various active oxygen species. Several substances other than luminol are also used for enhancement. Here, the term "luminol enhancing light emission" also includes light emission obtained by enhancement by substances other than luminol.

This method is simple, but requires to separate leukocytes from erythrocytes since light absorbance by erythrocytes must be prevented. The method for separating these blood cells is complicated and time-consuming. Furthermore, leukocytes largely change their state during the separation procedure, which raises the problem that the results of the measurement are not reliable.

To solve this problem, a method of measuring whole blood diluted to about to is proposed (Takayama, Eto, and Yamanaka, Standardization of Measurement of Oxidative Stress of Blood Samples by Detection of Luminol Enhancing Chemiluminescence—aiming at monitoring time course of in vivo oxidative stress—, Journal of Japanese Pharmacology 111(3), 177–186). However, dilution itself is thought to cause changes of the state of leukocytes. Furthermore, the dilution inevitably leads to considerable reduction of enhancement. The conventional methods cannot thus be effective for clinical and diagnostic use due to the above problems.

SUMMARY OF THE INVENTION

An objective of the present invention is to provide a method for measuring luminol enhancing light emission without separating leukocytes and erythrocytes, that is, using whole blood. This method is able to solve the problems attributable to the procedure for separating leukocytes from erythrocytes, to remarkably increase reliability of the measurement, and to considerably improve the measuring efficiency.

Considering protection by leukocytes against infection and damages of tissues, namely oxidative stress, the problems to be solved include not only the amount of active oxygen produced by leukocytes but also (1) how many leukocytes gather at the site of infection or are trapped by the capillary bed at that site, or (2) how long leukocytes take to pass through the capillary bed. In other words, a product of the amount of active oxygen produced by each leukocyte and the above (1) or (2) is considered to be a good index for ability to protect against infection and oxidative stress.

However, no effective method has been proposed so far for measuring the number of leukocytes trapped by the capillary bed or the time required for leukocytes to pass through the capillary bed.

Another object of the present invention is to provide a method for measuring a product of the amount of active oxygen produced by each leukocyte and the number of leukocytes trapped by the capillary bed or the time required for leukocytes to pass through the capillary bed to thereby provide an effective index for ability of leukocytes to protect against infection and oxidative stress caused by leukocytes.

A final object of the present invention is to improve the measurement efficiency so as to provide an effective measuring method which can be applied to clinical and diagnostic use.

A first aspect of the invention provides a method for measuring an amount of active oxygen produced by leukocytes and oxidative stress, wherein said method comprises allowing an anticoagulated whole blood sample collected from a human or an animal to flow in a microchannel array comprising a substrate with one or more fine channel arrays arranged on its surface and a transparent substrate which is adhered onto said substrate by contact bonding, and measuring a light emission level from whole leukocytes passing through said microchannel array through said transparent substrate to use the measured light emission level as an index of an amount of active oxygen produced by leukocytes and oxidative stress.

A second aspect of the invention provides the method according to the first aspect of the invention, wherein said light emission level is measured with or without stopping the flow of the whole blood.

A third aspect of the invention provides the method according to the first or second aspects of the invention, wherein a time-integral value of the measured light emission level is used as an index of an amount of active oxygen produced by leukocytes and of oxidative stress.

A fourth aspect of the invention provides the method according to any one of the first to third aspects of the invention, wherein a substance that amplifies light emission is added to the whole blood sample, and said whole blood sample is allowed to flow to measure the light emission level.

A fifth aspect of the invention provides the method according to any one of the first to fourth aspects of the invention, wherein a leukocyte-stimulating substance, a leukocyte-stimulating cell, or a leukocyte-stimulating particle is added to the whole blood sample, and said whole blood sample is allowed to flow to measure the light emission level.

A sixth aspect of the invention provides the method according to any one of the first to fifth aspects of the invention, wherein the light emission level is measured using a photomultiplier in combination with a direct current amplifier.

A seventh aspect of the invention provides the method according to any one of the first to fifth aspects of the invention, wherein the light emission level is measured using a photomultiplier in combination with a photoelectronic counter.

An eight aspect of the invention provides the method according to any one of the first to seventh aspects of the invention, wherein said method comprises providing a rotating stage on which plural microchannel array holders each of which is capable of holding the microchannel array can be mounted, allowing whole blood samples to flow in the plural microchannel arrays in turn, transferring said microchannel arrays onto said rotating stage to measure the light emission level in turn, and measuring the light emission level repeatedly from the first microchannel array when the measurement is done for the last microchannel array.

A ninth aspect of the invention provides a method for assessing an effect of a substance selected from the group consisting of drugs, foods, and substances made from their ingredients to enhance or suppress an amount of active oxygen produced by leukocytes and oxidative stress, wherein said method comprises allowing an anticoagulated whole blood sample collected from a human or an animal to flow in a microchannel array, measuring a light emission level from whole leukocytes passing through said microchannel array through said transparent substrate, allowing a whole blood sample to which said substance selected from the group has been added to flow in the array, measuring a light emission level from whole leukocytes passing through said microchannel array through said transparent substrate, and comparing the light emission levels between the whole blood sample with said substance selected from the group and the one without said substance selected from the group using the measured light emission levels as an index for an amount of active oxygen produced by leukocytes and for oxidative stress.

A tenth aspect of the invention provides a method for assessing an effect of a substance selected from the group consisting of drugs, foods, and substances made from their ingredients to enhance or suppress an amount of active oxygen produced by leukocytes and oxidative stress, wherein said method comprises allowing an anticoagulated whole blood sample collected from a human or an animal to flow in a microchannel array, measuring a light emission level from whole leukocytes passing through said microchannel array through said transparent substrate, allowing a whole blood sample collected from a human or an animal to which said substance selected from the group has been administered to flow in the microchannel array, measuring a light emission level from whole leukocytes passing through said microchannel array through said transparent substrate, and comparing the light emission levels between the whole blood sample with said substance selected from the group and the one without said substance selected from the group using the measured light emission levels as an index for an amount of active oxygen produced by leukocytes and for oxidative stress.

Explanation of Signs

11, substrate
12, transparent substrate
13, photomultiplier
14, leukocyte
15, erythrocyte
16, fine channel array (microchannel array)
17, small bank
18, terrace part
19, large bank
20, space (inlet and outlet of the microchannel array)
21, microchannel array holder
22, dark box case
23, shutter
24, photomultiplier
25, magnetic shield
26, direct current amplifier
27, recorder
31, rotating stage
32, pulse motor
33, dark box case
34, microchannel array holder
35, photomultiplier
36, pulse motor controller
37, amplifier

DETAITIED DESCRIPTION OF THE INVENTION

The present invention will be illustrated in detail below.

In the method of the present invention, light emission from leukocytes is measured based on luminol enhancing light emission. As described above, the luminol enhancing light emission method is performed by measuring faint light emitted from luminol when it is oxidized by various active oxygen species. Several substances other than luminol are also used for the purpose of enhancement. The term "luminol enhancing light emission" used herein includes all the cases using substances other than luminol.

First, the invention described in the first aspect of the invention is described.

The first aspect of the invention relates to a method for measuring an amount of active oxygen produced by leukocytes and oxidative stress, and is characterized by allowing an anticoagulated whole blood sample collected from a human or an animal to flow in a microchannel array, and measuring a light emission level from whole leukocytes passing through said microchannel array through the transparent substrate to use the measured light emission level as an index of an amount of active oxygen produced by leukocytes and oxidative stress.

The microchannel array used in the first aspect of the invention can be constructed by contact bonding of a transparent substrate onto the surface of a substrate where fine channel array is arranged.

Though materials for the substrate are not always particularly limited, silicon single crystal is preferably used since the fine channel array can be easily arranged on it.

On the surface of such a substrate made of silicon single crystal, various sizes of channel can be arranged by fine processing technique. The width or sectional area of the channel should be almost equal to the diameter or sectional area of the capillary. For example, if the microchannel array channel is made to have the channel with the width of 7 $\mu$m and the depth of 4.5 $\mu$m, it can be used as a model of the human capillary bed. Human whole blood is mainly described below as a test sample, but whole blood from an animal such as a dog or a cat can also be used.

In the first aspect of the invention, an anticoagulated whole blood sample collected from a human or an animal is first allowed to flow in the microchannel array described above.

Next, luminol enhancing light emission from whole leukocytes that are passing through the microchannel array is measured through the transparent substrate. The transparent substrate is thus preferably made of Pyrex® glass and the like material with excellent transparency.

The diameter or sectional area of human leukocytes is larger than the width or sectional area of the microchannel array. The leukocytes thus pass through the microchannel array with largely changing their shapes.

More specifically, leukocytes pass through the microchannel array with being strongly pressed on the transparent substrate. Therefore, erythrocytes cannot enter between leukocytes and the transparent substrate, and the light emitted from leukocytes by luminol enhancement to the direction of the transparent substrate is not absorbed by erythrocytes. This allows measuring luminol enhancing light emission from leukocytes through the transparent substrate without separating leukocytes from erythrocytes. The leukocytes trapped by the microchannel array do also not interfere the measurement. The light emission level can be measured using a photomultiplier in combination with a direct current amplifier as described in the sixth aspect of the invention. Alternatively, the measurement can be performed by the combination use of a photomultiplier and a photoelectronic counter as described in the seventh aspect of the invention.

The light emission level measured in the whole microchannel array is the product between the total number of leukocytes passed through the microchannel array or those trapped by the microchannel array and the average light emission level from each leukocyte. It is clear that this value is an index for the ability to protect against infection or for the oxidative stress.

The production of active oxygen by leukocytes gradually increases after leukocytes have been activated or have recognized stimulus. Having reached the maximal value, it gradually decreases. It is preferable to measure this time course. It usually takes 2 to 3 hours per sample.

As described in the eighth aspect of the invention, the time course of multiple samples can be measured by providing a rotating stage on which plural microchannel array holders each of which is capable of holding the microchannel array can be mounted, allowing whole blood samples to flow in the plural microchannel arrays in turn, transferring the microchannel arrays onto the rotating stage to measure the light emission level in turn, and measuring the light emission level repeatedly from the first microchannel array when the measurement is done for the last microchannel array.

More specifically, a number of the holders on each of which a microchannel array is set are prepared, multiple samples are measured in turn in a short period of time, and, turning back to the first sample, the measurement is repeatedly performed. This method makes it possible to measure the time course of multiple samples.

Such measurement is efficiently performed by constituting the rotating stage on which a number of holders are able to be mounted. Furthermore, the measurement efficiency can be remarkably improved.

As described in the ninth aspect of the invention, to assess an effect of a substance selected from the group consisting of drugs, foods, and substances made from their ingredients to enhance or suppress an amount of active oxygen produced by leukocytes and oxidative stress, an anticoagulated whole blood sample collected from a human or an animal is allowed to flow in the microchannel array, the light emission level from whole leukocytes passing through said microchannel array is measured through the transparent substrate, and a whole blood sample to which said substance has been added is allowed to flow in the array, the light emission level from whole leukocytes passing through the microchannel array is measured through the transparent substrate, and the light emission levels between the whole blood sample with said substance selected from the group and the one without said substance selected from the group are compared using the measured light emission levels as an index for an amount of active oxygen produced by leukocytes and oxidative stress. This method enables assessing an effect of a substance selected from the group consisting of drugs, foods, and substances made from their ingredients to enhance or suppress an amount of active oxygen produced by leukocytes and oxidative stress by adding said substance to a whole blood sample.

Examples of the drugs are a steroid agent and the like. Examples of foods include Kurozu, red wine, and the like. Examples of substances made from ingredients of drugs or foods are acetic acid, ethanol, and the like.

As described in the tenth aspect of the invention, an anticoagulated whole blood sample collected from a human or an animal is allowed to flow in the microchannel array, the light emission level from whole leukocytes passing through the microchannel array is measured through the transparent substrate, a whole blood sample derived from a human or an animal to which the substance selected from the group has been administered is allowed to flow in the microchannel array, the light emission level from whole leukocytes passing through the microchannel array is measured through the transparent substrate, and the light emission levels between the whole blood sample with the substance and the one without the substance are compared using the measured light emission levels as an index for an amount of active oxygen produced by leukocytes and for oxidative stress. This method enables assessing an effect of a substance selected from the group consisting of drugs, foods, and substances made from their ingredients to suppress an amount of active oxygen produced by leukocytes and oxidative stress by administering the substance to a human. Examples of drugs, foods, and substances made from their ingredients are as described above.

According to the invention described in the first aspect of the invention, faint light emission from leukocytes can be measured using a whole blood sample without separating leukocytes from erythrocytes.

This invention solves the problems attributed to a procedure for separating leukocytes from erythrocytes, remarkably increases reliability of the measurement, and considerably improves the measuring efficiency.

The invention described in the first aspect of the invention enables measuring the number of leukocytes trapped by the capillary bed or the time required for leukocytes to pass through the capillary bed, and thus provides a useful index for the ability to protect against infection and for oxidative stress.

Since the light emission from the whole microchannel array is measured in accordance with the invention described in the first aspect of the invention, the total light emission level is increased and can be measured using a direct current amplifier at real time. Therefore, the invention is advantageous in that the measurement can be performed when a whole blood sample is allowed to be flowing in the microchannel array without stopping the flow of the sample.

For this reason, when the measurement is performed using a photoelectronic counter with stopping the flow of a whole blood sample, the measuring enhancement increases, and the light emission from leukocytes can be measured without adding a leukocyte-stimulating substance, a leukocyte-stimulating cell, or a leukocyte-stimulating particle. In this case where a photoelectronic counter is used, the light emission from leukocytes can be measured advantageously without adding a sensitizer or an enhancer but by prolonging the counting time.

According to the invention described in the eighth aspect of the invention, it is possible to measure the time course of a number of samples, thereby remarkably increasing the measuring efficiency.

According to the invention described in the ninth aspect of the invention, an effect of a substance selected from the group consisting of drugs, foods, and substances made from their ingredients to enhance or suppress an amount of active oxygen produced by leukocytes and oxidative stress can be assessed.

The invention described in the tenth aspect of the invention also enables measuring an effect of a substance selected from the group consisting of drugs, foods, and substances made from their ingredients to enhance or suppress an amount of active oxygen produced by leukocytes and oxidative stress.

Therefore, the methods of the present invention can be useful for clinical or diagnostic use. If the measurement efficiency is further improved, the methods of the present invention would be extremely effective for clinical and diagnostic use.

The present invention will be demonstrated below with reference to Example depicted in Figures, but is not construed to be limited thereto.

EXAMPLE

Figure 1:
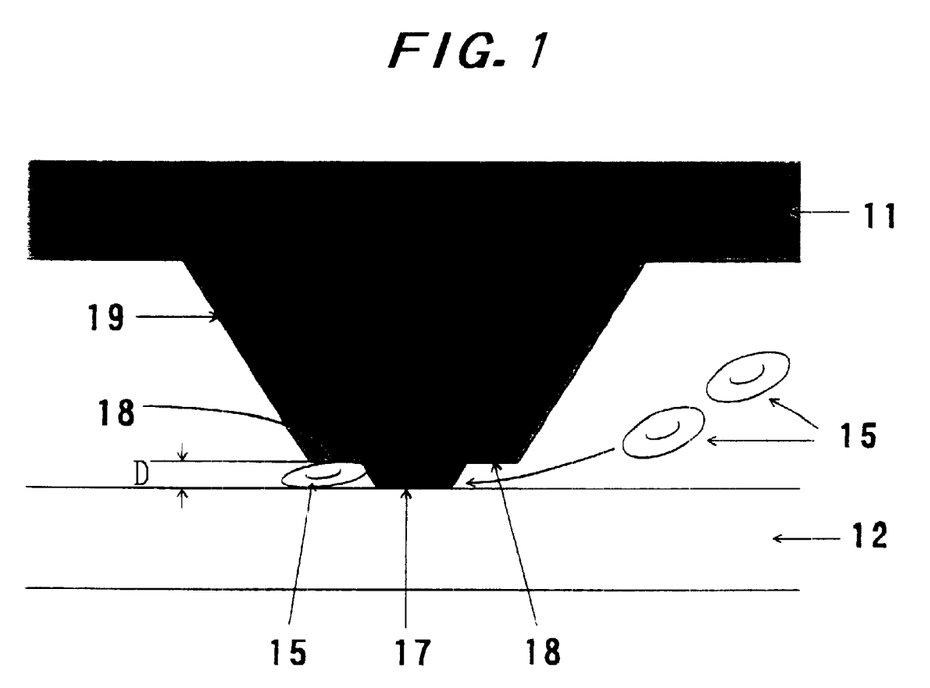
FIG. 1 shows an explanatory sectional view of the structure of the microchannel array that is a model for the capillary bed.
Figure 2:
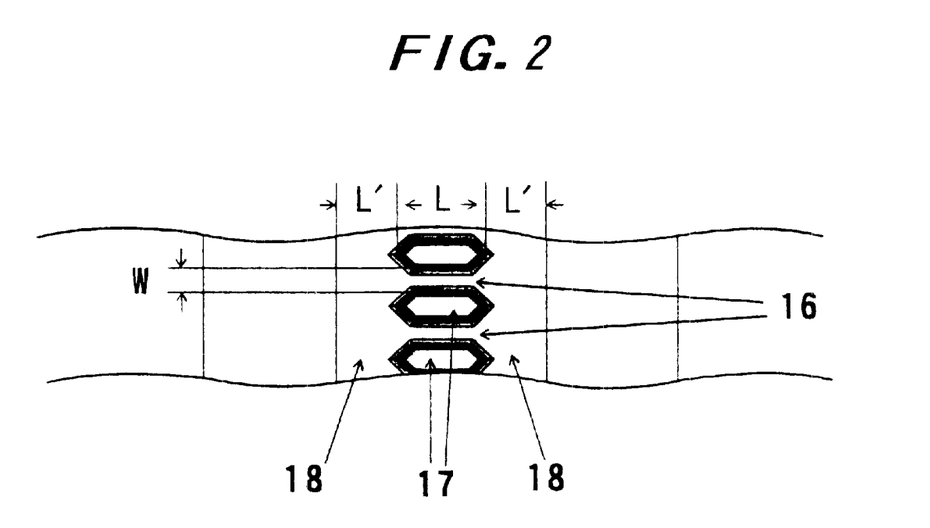
FIG. 2 shows an explanatory plane view of the substrate depicted in FIG. 1 from the side of the transparent substrate.

FIG. 1 shows a sectional view of the structure of the microchannel array that is a model for the capillary bed, in which the numeral 11 is a substrate made of silicon single crystal on the surface of which fine channel arrays are arranged. The numeral 12 is a transparent substrate, and the numeral 15 is erythrocyte. FIG. 2 is an explanatory plane view of the substrate 11 depicted in FIG. 1, seen from the side of the transparent substrate 12, in which the numeral 16 is a fine channel array. The numeral 17 is a small bank formed on the silicon single crystal substrate, the numeral 18 is a terrace part, and the numeral 19 is a big bank.

The transparent substrate 12 is adhered by contact bonding with the surface of the substrate 11 made of silicon single crystal where fine channel arrays 16 are arranged to provide the microchannel arrays.

The sectional shape of the thus-prepared microchannel array is generally a reverse trapezoid, but, without being limited thereto, can be a V-letter form or other shapes. The reverse trapezoid shape is formed by deepening the parts other than the microchannel array to minimize the flow resistance in the parts other than the microchannel array.

Figure 3:
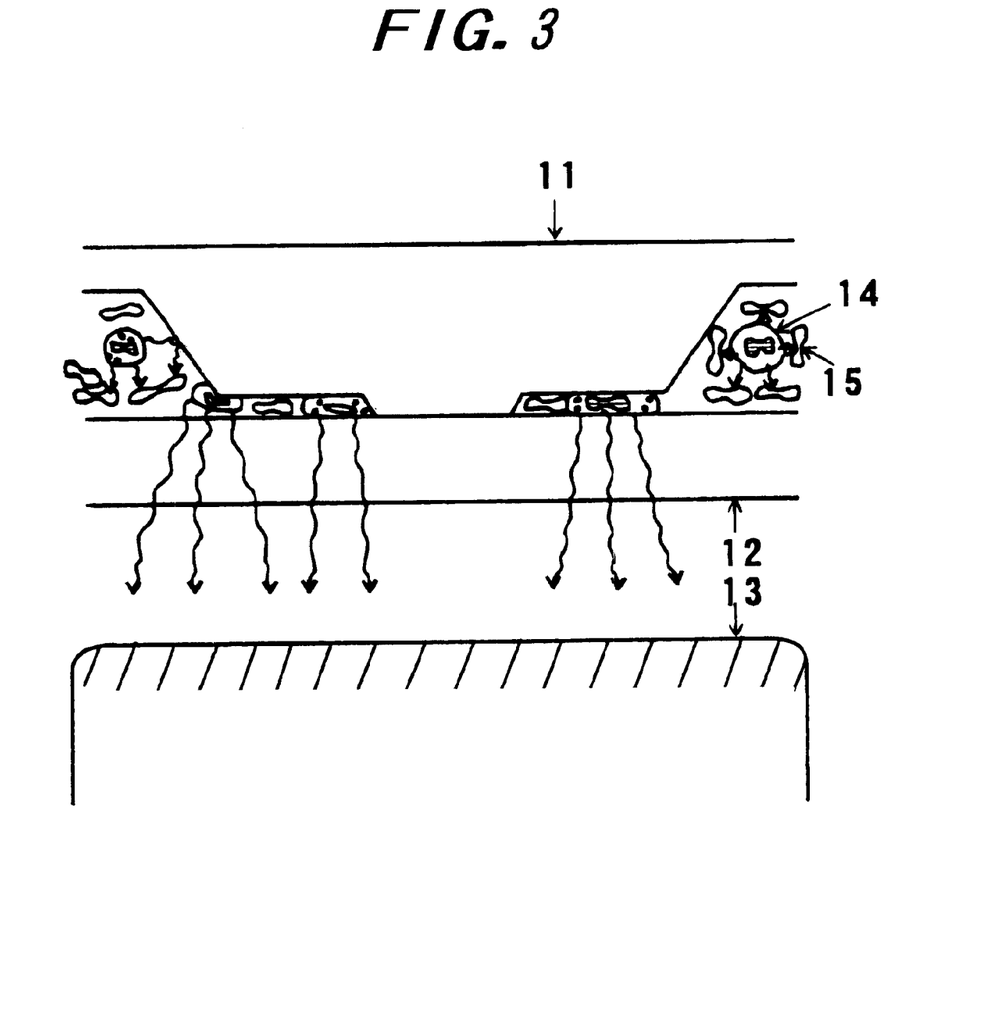
FIG. 3 shows the structure of the microchannel array that is a model for the capillary bed and the principle of the measurement of light emission from leukocytes without being affected by light absorbance by erythrocytes.

FIG. 3 is a figure demonstrating the structure of the microchannel array that is a model for the capillary bed and the principle of the measurement of light emission from leukocytes without being affected by light absorbance by erythrocytes. In FIG. 3, the numeral 13 is a photomultiplier, and the numeral 14 is a leukocyte.

The microchannel array that enables the measurement with high accuracy can be obtained by using silicon single crystal for the substrate 11 on which the fine channel array is arranged and using a glass substrate, particularly the one optically polished, as the transparent substrate 12 to be adhered by contact bonding with the substrate 11.

More specifically, the microchannel array 16 having the size of micron order can be arranged on the surface of the substrate 11 made of silicon single crystal with accuracy at the submicron level by means of photolithography and etching techniques. The one obtained as described above is used.

For example, the fine channel array 16 having the width of 7 $\mu$m is arranged on the silicon single crystal substrate having the size of 15 mm×15 mm×0.5 mm with accuracy at the submicron level by means of photolithography and etching techniques. The thus prepared substrate 11 on the surface of which the fine channel array is arranged is adhered by contact bonding with the transparent substrate 12 such as a glass substrate, thereby forming the microchannel array.

It is possible to use the microchannel array comprising a silicon substrate on the surface of which a fine channel is arranged and a glass substrate, which was developed by the present inventors previously (Unexamined Japanese Patent Publication No. Hei 2130471, U.S. Pat. No. 5,023,054 and Japanese Patent No. 2,532,707).

As the substrate made of silicon single crystal on the surface of which the fine channel array is arranged, the structure shown in FIGS. 1 and 2 particularly constitutes a highly practical microchannel array, which produces comparatively small flow resistance. In this structure, after the fine channel array 16 is arranged, the other parts are dug down deeply.

Consequently, the structure is made to have a large bank 19 and on its lower surface many small banks 17 arranged in parallel in the longitudinal direction.

The transparent substrate 12, preferably a glass substrate optically polished, is adhered by contact bonding on the substrate 11 made of silicon single crystal.

The upper surface of the small bank 17 arranged in parallel is the original surface of the substrate 11 made of silicon single crystal, which is not dug by etching. This surface is adhered with the transparent glass substrate 12.

The spaces between the small banks 17 are covered with the glass surface of the transparent glass substrate 12 to form fine arrays, that is, microchannel arrays.

The plane part before and behind the small banks 17 arranged in parallel constitutes the terrace part 18 common to the inlet and outlet of each channel. The spaces 20 between the large banks 19 connected to the plane part constitute wide passages which are import and export ducts for the microchannel arrays.

The substrate 11 made of silicon single crystal can be fused to the transparent substrate 12 by the anode contact method. Since the surfaces of the both substrates are optically polished, these are so tightly contacted with each other only by mechanical pressing that fluid can be prevented from leaking. In view of prevention of damages due to air bubbles and in view of washing, the contact tacking that allows the two substrates to be detachable is superior to the fusion.

Blood samples are allowed to flow in the thus-prepared microchannel arrays utilizing a difference in pressure.

When the distance D from the glass surface of the transparent substrate 12 to the bottom surface of each channel and the surface of the terrace part 18 is 4.5 $\mu$m, a leukocyte whose diameter is about 8 $\mu$m passes through the terrace part 18 with a flattened shape in the longitudinal direction. When the width W of the fine channel is 7 $\mu$m, leukocytes pass through the microchannel array (fine passage) with being flattened in not only the longitudinal direction but also the transverse direction. Wherever leukocytes flow in the channel, they pass through the channel with being strongly pressed on the glass surface of the transparent substrate 12. Thus, there is no space for erythrocytes entering between leukocytes and the glass surface of the transparent substrate 12. This means that the light emitted from leukocytes to the direction of the glass surface of the transparent substrate 12 immediately penetrate the transparent substrate 12 without being absorbed by erythrocytes. This way of flowing of leukocytes enables measuring the chemiluminescence from leukocytes when a whole blood sample is allowed to flow. The light emitted from leukocytes present in the places other than the microchannel array is not measured since it is absorbed by erythrocytes. As described above, FIG. 3 shows the structure of the microchannel array that is a model for the capillary bed and the principle of the measurement of light emission from leukocytes without being affected by light absorbance by erythrocytes.

Hence, the light emission level measured in the whole microchannel arrays is the product between the total number of leukocytes passed through the microchannel arrays or those trapped by the microchannel arrays and the average light emission level from each leukocyte.

The microchannel array can be considered as a model of the capillary bed of tissues. The measured light emission level is thus a suitable index for the ability to protect against infection and for oxidative stress. Furthermore, as described in the third aspect of the invention, the time-integral value of the measured light emission level can be a suitable index for an amount of active oxygen produced by leukocytes and for oxidative stress.

No one has performed so far the method in which the light emission level measured in the whole microchannel arrays is used as an index.

The light emission level can readily be measured in the whole microchannel arrays using a photomultiplier 13, for example, 8269 Model manufactured by Hamamatsu Photonics K.K.

The size of the silicon chip on which the microchannel array is arranged is usually about 15 mm square. The photomultiplier 13 having a light receiving surface with a diameter larger than the size of the silicon chip, for example, about 25 mm or more in the above case, is placed close to it. Such a photomultiplier can catch the light emission from the whole microchannel arrays in full. If necessary, the light can be gathered with a lens.

Figure 4:
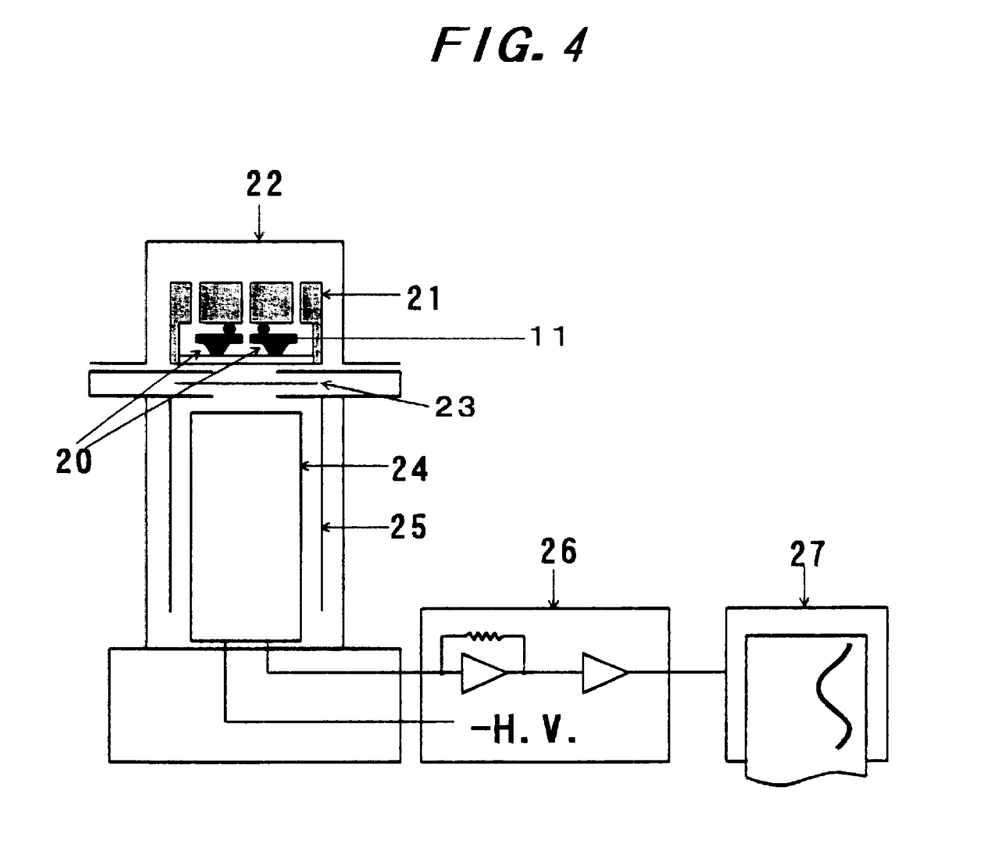
FIG. 4 shows an example of the constitution of the measuring system.

FIG. 4 shows one embodiment of the constitution of a measuring system.

The embodiment basically comprises a silicon single crystal substrate 11, a microchannel array holder 21 on which the substrate is set to prepare the microchannel array, a dark box 22 in which the above-described microchannel array is put to conduct measurement, a photomultiplier 24, a direct current amplifier 26 containing a high electric power source for the photomultiplier, and a recorder 27. In FIG. 4, the numeral 23 is a shutter, and the numeral 25 is a magnetic shield.

The photomultiplier 24 is set in the dark box 22. A lid or cap of the part where the microchannel array holder is to be set is constituted such that it does not open unless the shutter 23 placed in front of the light receiving surface of the photomultiplier 24 is closed. This constitution can prevent the photomultiplier 24 from getting the strong light, thereby preventing deterioration of the photomultiplier 24.

It is preferable to measure the light emission level by adding a substance capable of amplifying the light emission level, such as luminol, to a whole blood sample and allowing the whole blood sample to flow as described in claim 4.

The light emission from leukocytes is faint even if the enhancer is added and a photoelectronic counter is usually used for measuring it.

In this method that measures the light emission from the whole microchannel arrays, the total light emission level to be measured becomes high. The measurement can also thus be performed using the direct current amplifier 26. It means that the real time measurement is possible. The invention described in the sixth aspect of the invention is the method for measuring the light emission level using the photomultiplier 24 in combination with the direct current amplifier 26.

In this method, the measurement can be performed when a sample is flowing in the microchannel array. Using the photomultiplier 24 in combination with the direct current amplifier 26, the light emission is measured with or without stopping the flow of a sample, a whole blood sample, as described in the second aspect of the invention.

When the flow of a sample, a whole blood sample, is stopped, the measurement is preferably carried out using the photomultiplier 24 in combination with the photoelectronic counter (not shown in the figure) as described in the seventh aspect of the invention.

If the measurement is performed using the photoelectronic counter when the flow of the whole blood sample is stopped, the measuring enhancement increases and the light emission from leukocytes can be measured without adding any leukocyte-stimulating substance, leukocyte-stimulating cell, or leukocyte-stimulating particle. Usually, these substances are added to a whole blood sample followed by flowing the whole blood before the measurement as described in the fifth aspect of the invention.

The leukocyte-stimulating substance is the substance that activates leukocytes. Specific examples thereof include lipopolysaccharide (LPS), and phorbol myristate acetate (PMA), and the like. The leukocyte-stimulating cell is exemplified by various bacteria, and the leukocyte-stimulating particle is, for example, brushhight crystal.

If the counting period is prolonged in the photoelectronic counting method, the light emission from leukocytes can be measured without adding an enhancer to a whole blood sample. For clinical and diagnostic use, it would be important to carry out the measurement without using a leukocyte-stimulating substance, a leukocyte-stimulating cell, a leukocyte-stimulating particle (hereinafter sometimes referred to as a leukocyte-activating substance) or an enhancer.

Figure 5:
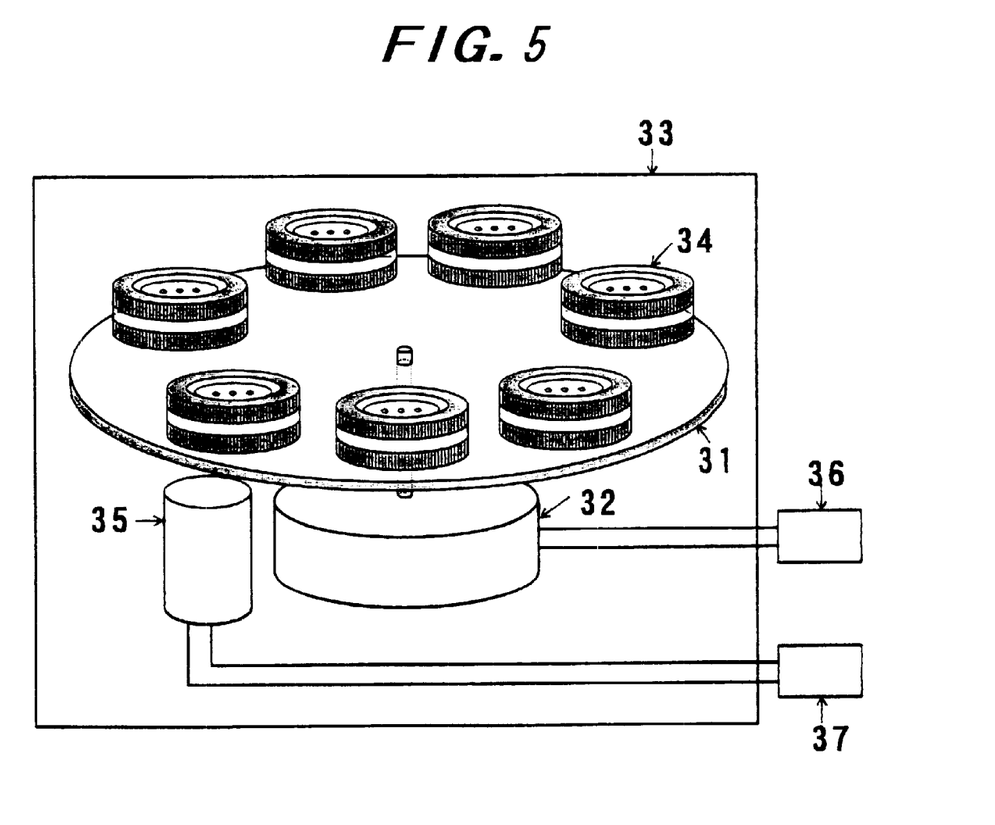
FIG. 5 shows a device suitable for the measurement of a number of samples.

FIG. 5 is a figure illustrating a device suitable for the measurement of a number of samples.

As described below, the production of active oxygen by leukocytes lasts for a long time. It is important to measure the time course, but it takes 2 to 3 hours for one sample.

Since the time course is relatively moderate, multiple microchannel array holders, that is, samples are repeatedly measured for a short period time with replacing one another to obtain the time course.

If the device as shown in FIG. 5 is used, the measurement can be performed for multiple microchannel array holders for a short period in turn.

More specifically, as described in the eighth aspect of the invention, the time course of multiple samples can be measured by providing a rotating stage 31 on which plural microchannel array holders 34 each of which is capable of holding the microchannel array can be mounted, allowing whole blood samples to flow in the plural microchannel arrays in turn, transferring said microchannel arrays onto the rotating stage to measure the light emission level in turn, and measuring the light emission level repeatedly from the first microchannel array when the measurement is done for the last microchannel array. Incorporation of the rotating stage 31 on which plural holders can be mounted enables such an efficient measurement. The measurement efficiency is thus remarkably improved. In FIG. 5, seven microchannel array holders 34 are mounted on the rotating stage 31, but any plural holders can be mounted without limitation. In FIG. 5, the numeral 32 denotes a pulse motor; 33, a dark box; 35, a photomultiplier; 36, a pulse motor controller; and 37, an amplifier.

Figure 6:
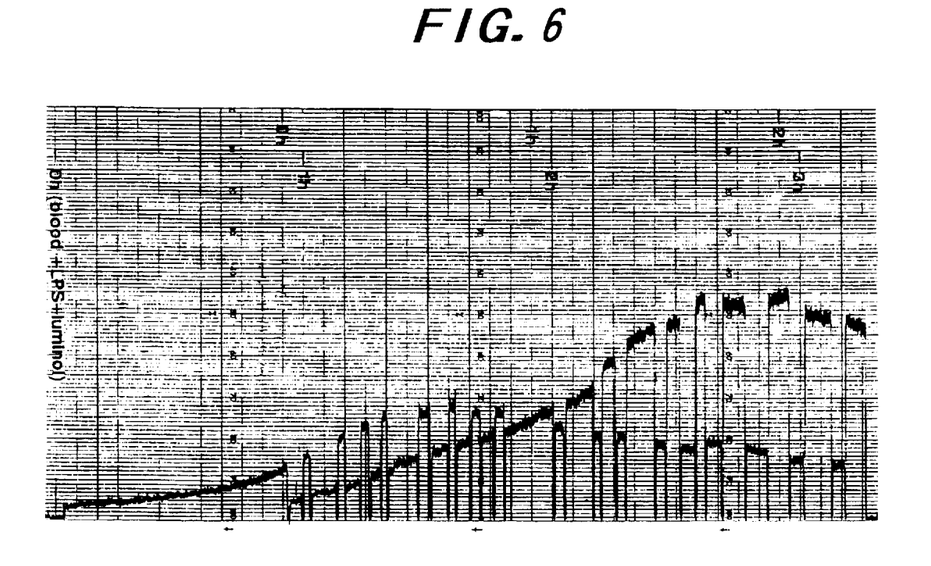
FIG. 6 is a graph showing an example of time course of the light emission level measured in Example. The X- and Y-axes denote time and the light emission level, respectively.

FIG. 6 is an example of a measuring result. It shows the time course of the light emission level. As described in the third aspect of the invention, the integral value of the time course of the light emission level as shown in FIG. 6 is calculated according to the method of the present invention to be used as an index for an amount of active oxygen produced by leukocytes and for oxidative stress.

Specifically, a whole blood sample is collected from a healthy volunteer with a syringe containing heparin (using 1000 unit/ml of a heparin solution in an amount of 5% of the blood volume), 100 ng/ml of LPS as a leukocyte-activating substance and 200 $\mu$M of luminol as an enhancer were added, the whole blood sample was allowed to flow in the microchannel array with 20 cm of water head difference. When 100 $\mu$l of the blood flowed, the flow was stopped and the microchannel array holder was put into a dark box as shown in FIG. 4 to measure the light emission.

After leukocytes are exposed to a leukocyte-activating substance such as LPS, the amount of active oxygen produced by leukocytes, i.e., the light emission level, gradually increases with the passage of time, reaches the peak in one to two hours, and thereafter gradually decreases as shown in FIG. 6. To measure the peak, the time course has to be monitored for more than two hours. If one sample is measured for two hours or longer and then the second sample is measured, the measurement efficiency is remarkably reduced.

Since the time course gradually changes, samples can be measured alternately without replacing them but using the above described two or more microchannel array holders as shown in FIG. 5. FIG. 6 shows the result obtained by alternately measuring samples using a device comprising a rotating stage on which two microchannel array holders are mounted. The second sample is a whole blood sample collected from the same subject 30 minutes after the subject was given about 10 ml of Kurozu. The second sample shows an increase of the amount of active oxygen produced.

The result indicates that the time course of the light emission level of a number of samples can be measured without reducing accuracy by repeating the procedure that comprises measuring multiple samples on the microchannel array holders in turn at intervals of several minutes using a device with a rotating stage as shown in FIG. 5.

Figure 7:
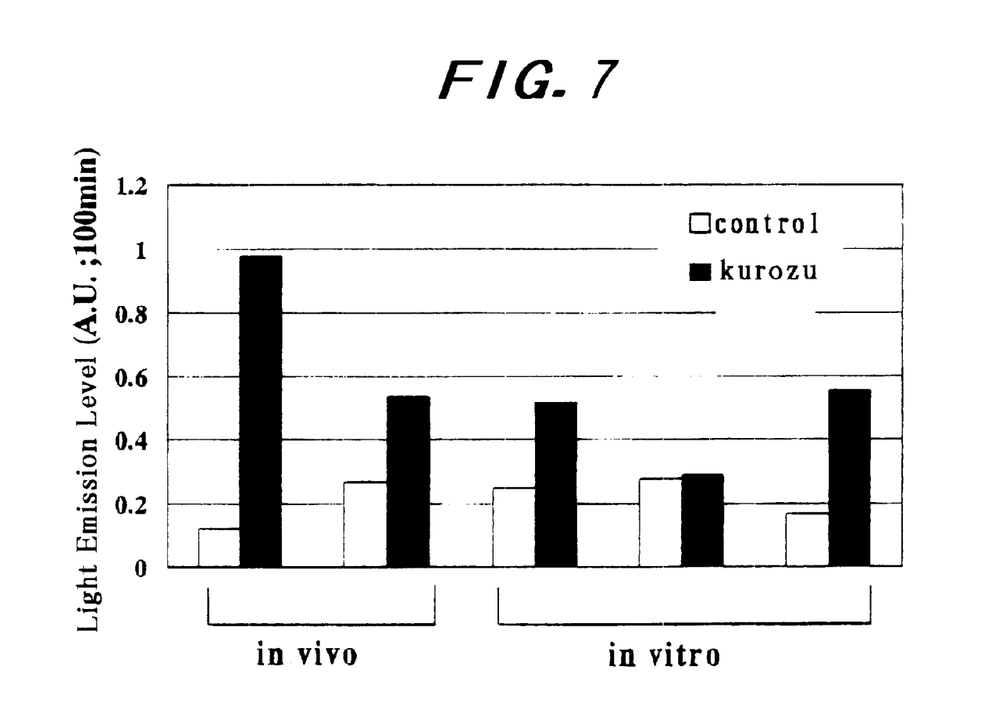
FIG. 7 is a graph showing the comparison of the light emission levels 100 minutes after the commencement of the measurement between a whole blood sample from the subject who was given Kurozu (Japanese traditional vinegar) and a whole blood sample to which Kurozu was added.

FIG. 7 is a graph showing the comparison of the light emission level 100 minutes after the commencement of the measurement between a whole blood sample from the subject who was given Kurozu and a whole blood sample to which Kurozu was added.

In FIG. 7, data of Kurozu among in vivo data were obtained by collecting a whole blood sample with a heparin-containing syringe (using 1000 unit/ml of a heparin solution in an amount of 50 of the blood volume) from a healthy subject who was given about 10 ml of Kurozu, adding to the whole blood sample 100 ng/ml of LPS as a leukocyte-activating substance and 200 $\mu$M of luminol as an enhancer, allowing the sample to flow in the microchannel arrays with 20 cm of difference in water head, stopping the flow when 100 $\mu$l of the sample flowed, transferring the microchannel array holder into a dark box as shown in FIG. 4, and measuring the light emission level. In this case, data of control was obtained by measuring a whole blood sample collected from the same subject before the intake of Kurozu in the same manner as described above.

In FIG. 7, data of Kurozu among the in vitro data were obtained by collecting a whole blood sample with a heparin-containing syringe (using 1000 unit/ml of a heparin solution in an amount of 5% of the blood volume) from a healthy subject, adding to the whole blood sample 100 ng/ml of LPS as a leukocyte-activating substance and 200 $\mu$M of luminol as an enhancer, further adding Kurozu in an amount of 1/2000 volume of the whole blood sample, allowing the sample to flow in the microchannel arrays with 20 cm of water head difference, stopping the flow when 100 $\mu$l of the sample flowed, transferring the microchannel array holder into a dark box as shown in FIG. 4, and measuring the light emission level. In this case, data of control was obtained by measuring a whole blood sample collected in the same manner as described above except that Kurozu was not added to the whole blood sample.

From FIG. 7, it can be understood that the light emission level was increased in both of the case where about 10 ml of Kurozu was given (in vivo) to the subject and the case where Kurozu was added to the whole blood sample in amount of 1/2000 volume thereof.

Kurozu is considered to a food that increases a deformation ability of erythrocytes and has finctions to improve circulation. An effect of said food to enhance or suppress an amount of active oxygen produced by leukocytes and oxidative stress can be assessed by measuring the light emission before and after the food is given to a human or an animal according to the method of the present invention. As for Kurozu, it is judged that it can increase an amount of active oxygen produced by leukocytes and oxidative stress.

It is possible to assess whether various drugs or their ingredients as well as foods such as Kurozu can enhance or suppress an amount of active oxygen produced by leukocytes and oxidative stress.

As described in the ninth aspect of the invention, an effect of a substance to enhance or a suppress an amount of active oxygen produced by leukocytes and oxidative stress can be assessed by measuring the light emission level before and after the substance to be tested is added to a whole blood sample. In addition, as described in the tenth aspect of the invention, such an assessment can be effected by measuring the light emission level before and after a substance selected from the group consisting of drugs, foods, and substances made from their ingredients is given to a human or an animal.

What is claimed is:

1. A method for measuring an amount of active oxygen produced by leukocytes and oxidative stress, wherein said method comprises allowing an anticoagulated, undiluted whole blood collected from a human or an animal to pass through a microchannel array comprising a channeled substrate with one or more channel arrays arranged on its surface and a transparent substrate bonded to said channeled substrate, and measuring through said transparent substrate a light emission level from whole leukocytes passing through said microchannel array to use the measured light emission level as an index of an amount of active oxygen produced by leukocytes and oxidative stress.

2. The method according to claim 1, wherein said light emission level is measured with or without stopping the flow of the whole blood sample.

3. The method according to claims 1 or 2, wherein the light emission level is measured using a photomultiplier in combination with a direct current amplifier.

4. The method according to claim 3, wherein said method comprises providing a rotating stage on which plural microchannel array holders each of which is capable of holding the microchannel array can be mounted, allowing whole blood samples to flow in plural microchannel arrays in turn, transferring said microchannel arrays onto said rotating stage to measure the light emission level in turn, and measuring the light emission level repeatedly from a microchannel array when the measurement is done for the previous microchannel array on the rotating stage.

5. The method according to claim 3, wherein a substance that amplifies light emission is added to the whole blood sample, and then said whole blood sample is allowed to flow in the microchannel array to measure the light emission level.

6. The method according to claim 3, wherein a leukocyte-stimulating substance, a leukocyte-stimulating cell, or a leukocyte-stimulating particle is added to the whole blood sample, and then said whole blood sample is allowed to flow in the microchannel array to measure the light emission level.

7. The method according to claims 1 or 2, wherein the light emission level is measured using a photomultiplier in combination with a photoelectronic counter.

8. The method according to claim 7, wherein said method comprises providing a rotating stage on which plural microchannel array holders each of which is capable of holding the microchannel array can be mounted, allowing whole blood samples to flow in plural microchannel arrays in turn, transferring said microchannel arrays onto said rotating stage to measure the light emission level in turn, and measuring the light emission level repeatedly from a microchannel array when the measurement is done for the previous microchannel array on the rotating stage.

9. The method according to claim 7, wherein a substance that amplifies light emission is added to the whole blood sample, and then said whole blood sample is allowed to flow in the microchannel array to measure the light emission level.

10. The method according to claim 7, wherein a leukocyte-stimulating substance, a leukocyte-stimulating cell, or a leukocyte-stimulating particle is added to the whole blood sample, and then said whole blood sample is allowed to flow in the microchannel array to measure the light emission level.

11. A method for assessing an effect of a substance selected from the group consisting of drugs, foods, and substances made from ingredients of drugs and ingredients of foods to enhance or suppress an amount of active oxygen produced by leukocytes and oxidative stress, wherein said method comprises allowing a first sample of anticoagulated, undiluted whole blood collected from a human or an animal to flow in a microchannel array comprising a channeled substrate with one or more channel arrays arranged on its surface and a transparent substrate bonded to said channeled substrate, measuring through said transparent substrate a light emission level from said first sample from whole leukocytes passing through said microchannel array, allowing a second sample of said anticoagulated, undiluted whole blood to which said substance selected from the group has been added to flow in the microchannel array, measuring through said transparent substrate a light emission level from said second sample from whole leukocytes passing through said microchannel array, and comparing the light emission levels from said first sample and said second sample using the measured light emission levels as an index for the effect of the substance selected from the group consisting of drugs, foods, and substances made from ingredients of drugs and ingredients of foods to enhance or suppress an amount of active oxygen produced by the leukocytes of the blood sample and oxidative stress.

12. A method for assessing an effect of a substance selected from the group consisting of drugs, foods, and substances made from ingredients of drugs and ingredients of foods to enhance or suppress an amount of active oxygen produced by leukocytes and oxidative stress, wherein said method comprises allowing a first sample of anticoagulated, undiluted whole blood collected from a human or an animal to flow in a microchannel array comprising a channeled substrate with one or more channel arrays arranged on its surface and a transparent substrate bonded to said channeled substrate;

measuring through said transparent substrate a light emission level from said first sample from whole leukocytes passing through said microchannel array;

allowing a second sample of said anticoagulated, undiluted whole blood, collected from said human or said animal after said substance selected from the group has been administered in vivo, to flow in the microchannel array;

measuring through said transparent substrate a light emission level from said second sample from whole leukocytes passing through said microchannel array; and comparing the light emission levels from said first sample and said second sample using the measured light emission levels as an index for the effect of the substance selected from the group consisting of drugs, foods, and substances made from ingredients of drugs and ingredients of foods to enhance or suppress an amount of active oxygen produced by the leukocytes of the blood sample and oxidative stress.

* * * * *